(12) United States Patent
Ohashi et al.

(10) Patent No.: US 7,794,655 B2
(45) Date of Patent: Sep. 14, 2010

(54) TEST FLUID MEASUREMENT DEVICE AND SENSITIVITY CALIBRATION METHOD THEREOF

(75) Inventors: Akio Ohashi, Tokyo (JP); Satoshi Ikeda, Tokyo (JP)

(73) Assignee: Tanita Corporation, Tokyo (JP)

( * ) Notice: Subject to any disclaimer, the term of this patent is extended or adjusted under 35 U.S.C. 154(b) by 229 days.

(21) Appl. No.: 11/956,921

(22) Filed: Dec. 14, 2007

(65) Prior Publication Data

US 2008/0159914 A1 Jul. 3, 2008

(30) Foreign Application Priority Data

Dec. 20, 2006 (JP) .............................. 2006-342034
Sep. 14, 2007 (JP) .............................. 2007-239893

(51) Int. Cl.
| | |
|---|---|
| G01N 15/06 | (2006.01) |
| G01N 27/00 | (2006.01) |
| G01N 27/26 | (2006.01) |
| G01N 1/00 | (2006.01) |
| C12M 1/00 | (2006.01) |
| C12N 9/00 | (2006.01) |
| C12N 11/00 | (2006.01) |
| C25B 9/00 | (2006.01) |
| C25B 11/00 | (2006.01) |
| C25B 13/00 | (2006.01) |

(52) U.S. Cl. .................... 422/68.1; 422/82.01; 204/400; 204/403.01; 204/406

(58) Field of Classification Search ........................ None
See application file for complete search history.

(56) References Cited

U.S. PATENT DOCUMENTS

| 4,420,564 A | 12/1983 | Tsuji et al. |
| 4,436,812 A * | 3/1984 | Endoh et al. ................... 435/14 |
| 4,935,106 A * | 6/1990 | Liston et al. ................. 204/400 |
| 7,041,206 B2 * | 5/2006 | Gephart et al. .............. 204/406 |
| 2002/0014409 A1 * | 2/2002 | Matsumoto et al. ......... 204/403 |
| 2003/0062262 A1 | 4/2003 | Mansouri et al. |
| 2004/0086427 A1 * | 5/2004 | Childers et al. ............. 422/100 |
| 2004/0132193 A1 | 7/2004 | Frischauf et al. |

FOREIGN PATENT DOCUMENTS

| GB | 2183041 | 5/1987 |
| JP | H09-297120 | 11/1997 |
| JP | 2004-233294 | 8/2004 |
| WO | WO 99/13100 | 3/1999 |
| WO | WO 01/67079 | 9/2001 |

* cited by examiner

*Primary Examiner*—Jill Warden
*Assistant Examiner*—Charles Hammond
(74) *Attorney, Agent, or Firm*—Paul F. Neils, Esq.; Akerman Senterfitt

(57) ABSTRACT

A test fluid measurement device includes an output acquisition unit for acquiring an output value from a urinary sugar sensor, when a reference fluid, set to a specified density, is applied to the urinary sugar sensor. By using this output value to set a reference value, a reference value setting unit calibrates the sensitivity of the urinary sugar sensor. During sensitivity calibration, an output value judgment unit determines according to an output value that is already acquired by the output acquisition unit whether or not the output value that is newly acquired by the output acquisition unit is suitable to be set as the reference value. After an output value is determined not to be suitable as the reference value setting, a reference fluid detection unit detects when more reference fluid from which another output value is to be acquired by the output acquisition unit has been additionally applied.

20 Claims, 7 Drawing Sheets

TEST FLUID MEASUREMENT DEVICE AND SENSITIVITY CALIBRATION METHOD THEREOF

FIELD OF THE INVENTION

The present invention relates to a test fluid measurement device and sensitivity calibration method thereof that uses a reference fluid having a certain substance that is set to a specified density in order to calibrate the sensitivity of a biosensor that measures the amount of the certain substance that is contained in a test fluid.

BACKGROUND OF THE INVENTION

A known example of this kind of measurement device that requires calibration of its biosensor, is a urine measurement device that measures the urinary sugar level of urine that is directly applied to the biosensor during urination (refer to Japanese patent application H9-297120). In other words, since the sensitivity of the biosensor changes according to the amount of time elapsed, frequency of use such as the number of times used or length of time used, or the environment such as temperature or storage conditions, it becomes necessary to calibrate the reference value that becomes a reference during measurement (hereafter, referred to as the 'measurement reference value').

Generally, this kind of measurement device determines whether or not calibration of the sensitivity is necessary according to the frequency of use of the biosensor, and when calibration is necessary, notifies and prompts the user to perform calibration. In this calibration of the sensitivity, output from the biosensor for a reference fluid is obtained. That is, when measuring a reference fluid, the user drips some reference fluid from a dropper shaped container onto the biosensor, and the output from the biosensor after doing this is obtained by the measurement device that comprises that biosensor.

After measuring this reference fluid, it is necessary that the biosensor, (1) first, be cleaned in a cleaning fluid, (2) then immersed in a preservative fluid such as a buffer fluid, and (3) allowed time for the baseline of the output to become stable. (Hereafter, the process of these steps (1) to (3) will be referred to as the 'cleaning process'.)

However, normally, sensitivity calibration is seldom completed after one measurement of the reference fluid. For example, when only a small amount of reference fluid that is applied to the biosensor, that amount might not be enough to satisfy the required amount needed for measurement. In that case, the output value from the biosensor is not used for sensitivity calibration and the measurement device displays a message that measurement of the reference fluid must be performed again.

Despite this, the cleaning process was performed each time the reference fluid was applied. This is so that no reference fluid remains in the biosensor in order that the measurement of the reference fluid performed next will be performed under the same measurement conditions. In this kind of sensitivity calibration, the work of performing the cleaning process must be performed, which takes time.

SUMMARY OF THE INVENTION

The object of the present invention is to provide a test fluid measurement device and sensitivity calibration method capable of calibrating the sensitivity of a biosensor easily and in a short amount of time.

The test fluid measurement device according to the invention comprises an output acquisition means and a setting means. The output acquisition means acquires the output value of a biosensor that measures the amount of a certain substance that is contained in a test fluid when a reference fluid containing the certain substance that is set to a specified density is applied to the biosensor. The setting means calibrates the sensitivity of the biosensor by setting a reference value that will be a reference for measurement by the biosensor using the output value that was acquired from the biosensor by the output acquisition means.

The test fluid measurement device also comprises a judgment means and a detection means. This judgment means uses an output value that is already acquired from the biosensor by the output acquisition means for determining whether or not an output value that is newly acquired from the biosensor by the output acquisition means during sensitivity calibration by the setting means is suitable to be used as the setting for the reference value. The detection means detects when the reference fluid, which is the subject of acquiring another output value by the output acquisition means, is additionally applied to the biosensor after the judgment means determines that an output value is not suitable as the setting for the reference value.

The setting means sets the output value from the biosensor, which was determined by the judgment means to be suitable as the setting for the reference value, as the reference value.

The setting means is constructed as follows: the setting means sets the average of the output values, which were acquired by the output acquisition means a specified number of times and were determined by the judgment means to be suitable as the setting for the reference value, as the reference value.

The judgment means is constructed as follows: the judgment means determines that the output value from the biosensor that was acquired the first time by the output acquisition means during the sensitivity calibration by the setting means is not suitable as the setting for the reference value.

The detection means is constructed as follows: the detection means detects that the reference fluid has been additionally applied to the biosensor due to change in the output value from the biosensor that is acquired by the output acquisition means.

The test fluid measurement device further comprises temperature detection means for detecting the temperature of the biosensor. In this case, the detection means detects that the reference fluid has been additionally applied to the biosensor due to change in the temperature of the biosensor that is detected by the temperature detection means.

The test fluid measurement device further comprises impact detection means for detecting physical impact that is applied to the biosensor. In this case, the detection means detects that the reference fluid has been additionally applied to the biosensor due to impact to the biosensor that is detected by the impact detection sensor.

The test fluid measurement device further comprises addition confirmation means for a user to input confirmation that the reference fluid has been additionally applied to the biosensor. In this case, the detection means detects that the reference fluid has been additionally applied to the biosensor due to the addition confirmation that is input from the addition confirmation means.

The output acquisition means has two operating states: a non-acquisition state and an acquisition state. The non-acquisition state is a state in which the output value from the biosensor is not acquired even though the reference fluid is applied, and the acquisition state is a state in which the output value from the biosensor is acquired when the reference fluid is applied. Here, an instruction input means is used for a user to input an instruction to change the operating state of the output acquisition means from the non-acquisition state to the acquisition state. The output acquisition means changes the operating state from the non acquisition state to the acquisition state based on the change instruction that is input from this instruction input means.

The output acquisition means acquires an output value from the biosensor after a specified amount of time has elapsed from the instant when the operating state of the output acquisition means changes from the non-acquisition state to the acquisition state.

The test fluid measurement further comprises notification means for notifying that the operating state of the output acquisition means is either the non-acquisition state or the acquisition state.

A sensitivity calibration method for calibrating the sensitivity of a biosensor comprises the steps of acquiring the output value of a biosensor that measures the amount of a certain substance that is contained in a test fluid when a reference fluid containing the certain substance that is set to a specified density is applied to the biosensor, and setting a reference value that will be a reference for measurement by the biosensor using the acquired output value.

During sensitivity calibration, the sensitivity calibration method: (1) uses an output value that has already been acquired to determine whether or not an output value that is newly acquired from the biosensor is suitable to be used as the setting for the reference value; and (2) detects when the reference fluid, which is the subject of acquiring another output value, is additionally applied to the biosensor after an output value is determined not to be suitable as the setting for the reference value.

With the test fluid measurement device of the invention, when it is determined during sensitivity calibration of the biosensor that an output value from the biosensor is not suitable as the setting for the reference value (measurement reference value), after that, the additional application of more reference fluid is detected without performing the cleaning process. Also, after the reference fluid has been additionally applied, another output value from the biosensor is acquired.

Therefore, compared with a conventional measurement device in which the cleaning process was always performed after an output value was obtained, the device of the present invention is capable of performing sensitivity calibration of a biosensor more easily and in a shorter period of time.

DETAILED DESCRIPTION OF THE INVENTION

The preferred embodiments of the invention will be explained with reference to the drawings.

Embodiment 1

Figure 1:
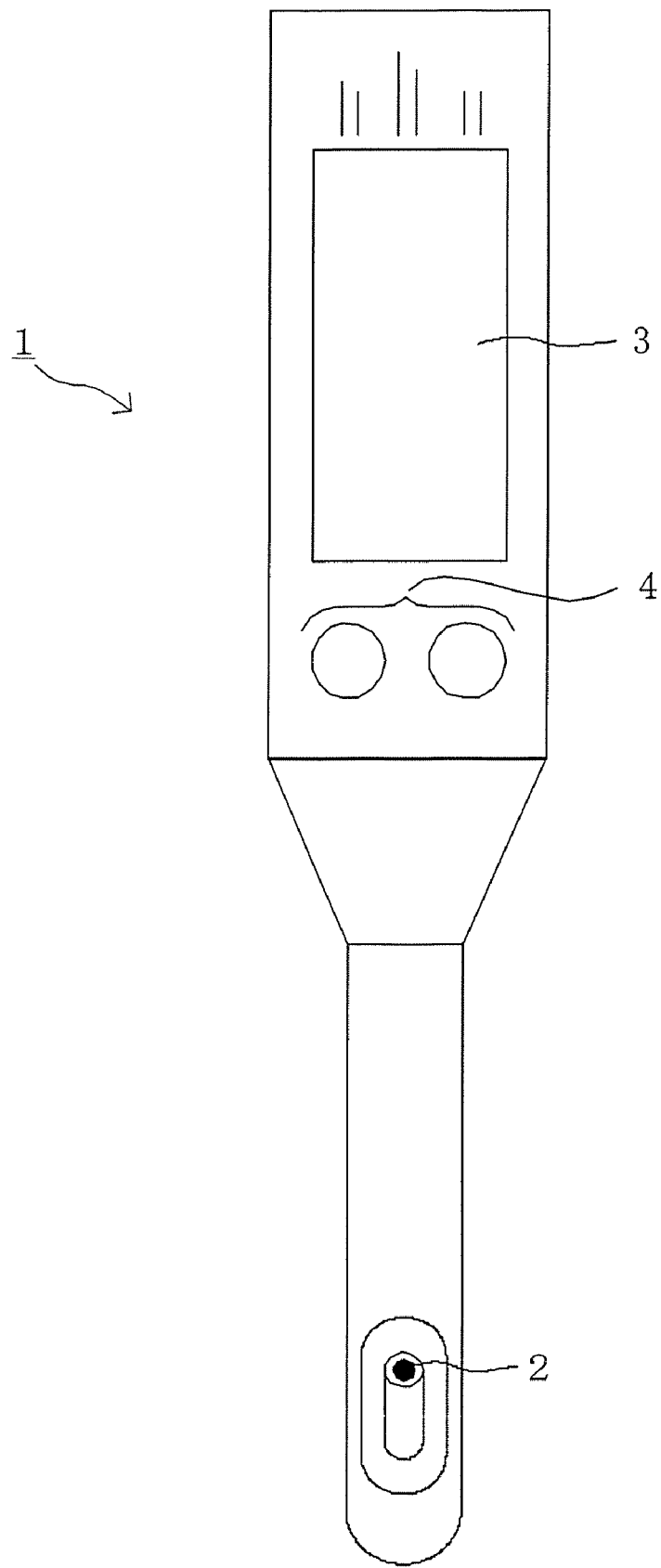
FIG. 1 is a drawing showing the external appearance of a urinary sugar meter of a first embodiment of the invention.
Figure 2:
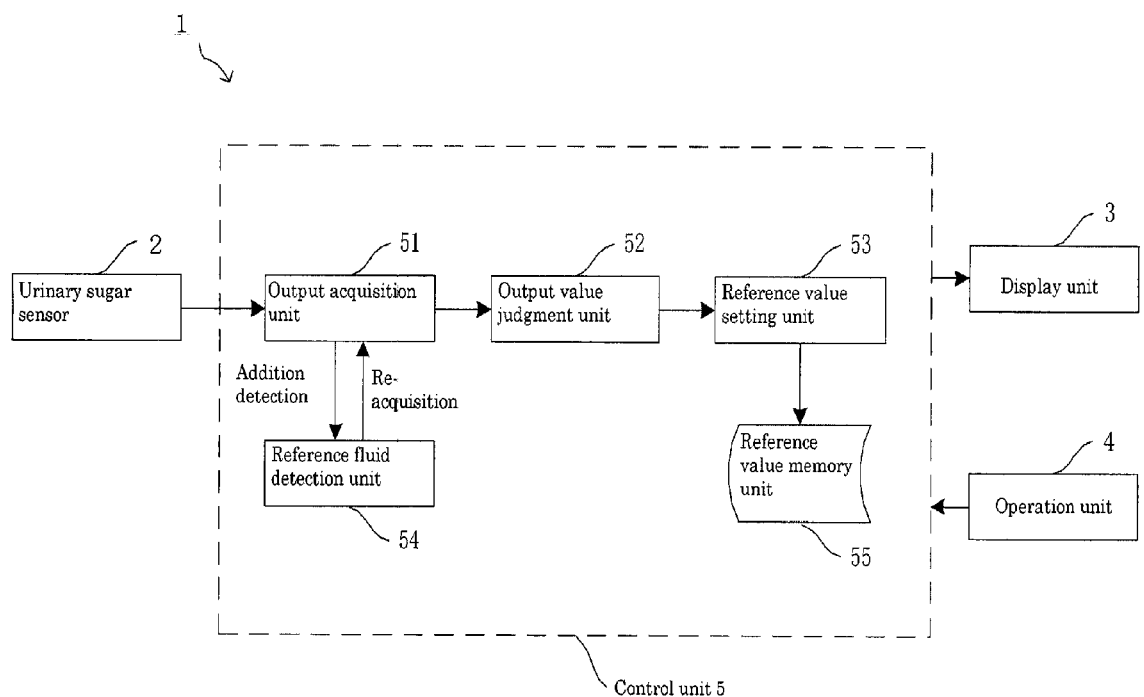
FIG. 2 is a block diagram showing the construction of the electrical circuits for sensitivity calibration of the urinary sugar meter.

As a first embodiment of the invention, a urinary sugar meter 1, which is a test fluid measurement device that uses a urinary sugar sensor as the biosensor, will be explained. As shown in FIG. 1 and FIG. 2, the urinary sugar meter 1 comprises: a urinary sugar sensor 2, a display unit 3, an operation unit 4 and a control unit 5. The urinary sugar sensor 2 electrochemically detects (measures) the amount of sugar content in the urine of the test fluid. The part surrounding this urinary sugar sensor 2 is concave shaped so that it can hold the reference fluid. The urinary sugar sensor 2 is located at the bottom of this concave shaped section.

The display unit 3 displays measurement values, judgment results and operation guidance. The operation unit 4 includes a power ON/OFF switch, and by pressing the power ON/OFF switch the power to the urinary sugar meter 1 is turned from OFF to ON, and by pressing the power ON/OFF switch again, the power to the urinary sugar meter is turned OFF.

The control unit 5 comprises a CPU, RAM, ROM, EPROM, input/output interface and the like, and performs overall control of the urinary sugar meter, including the display on the display unit 3 and input from the operation unit 4. In addition, the urinary sugar meter 1 comprises an A/D conversion unit (not shown in the figure), and that A/D conversion unit converts the signal that is detected by the urinary sugar sensor 2 to digital data and outputs the result to the control unit 5.

More specifically, the urinary sugar meter 1 has a measurement mode for measuring the urinary sugar level, and a calibration mode for calibrating the sensitivity of the urinary sugar sensor 2, and the control unit 5 is capable of switching between the measurement mode and the calibration mode.

The control unit (CPU) 5 comprises a urinary sugar measurement unit and a counter that are used in the measurement mode of the urinary sugar meter 1. The urinary sugar measurement unit performs overall control of the measurement of the urinary sugar level in the measurement mode, and the counter counts the number of times that the urinary sugar measurement unit has measured the urinary sugar level as a value that corresponds to the frequency of use of the urinary sugar sensor 2. Furthermore, when the number of times that the urinary sugar level has been measured, which is counted by the counter, reaches a specified number of times, the urinary sugar meter 1 determines that 'calibration is necessary', and displays a message on the display unit 3 indicating that calibration is necessary and to change to the calibration mode.

The functions that are realized in the calibration mode of the urinary sugar meter 1 when the control unit 5 executes programs are shown in FIG. 2 as a block diagram. The programs that are executed here make each of the functions possible, including an output acquisition unit 51, an output value judgment unit 52, a reference value setting unit 53 and a reference fluid detection unit 54. (Naturally, part of these units 51 to 54 can also be constructed using electrical circuits.)

In the calibration mode, the output acquisition unit 51 acquires the output value from the urinary sugar sensor 2 by way of the A/D conversion unit when a reference fluid, whose urinary sugar content has a set density, is applied to the urinary sugar sensor 2. The output value judgment unit 52 then determines whether or not the output value that is newly acquired from the urinary sugar sensor 2 by the output acquisition unit 51 is suitable as the setting for the measurement reference value (that will be the reference when performing measurement by the urinary sugar sensor 2) based on an output value that has already been acquired from the urinary sugar sensor 2 by the output acquisition unit 51.

The reference value setting unit 53 calibrates the sensitivity of the urinary sugar sensor 2 by setting the measurement reference value using the output value from the urinary sugar sensor 2 that was determined to be suitable as the setting for the measurement reference value. This measurement reference value is stored in a reference value memory unit 55 in the EPROM. The measurement reference value for measurement of the urinary sugar level in the measurement mode is stored in the reference value memory unit 55 before the urinary sugar meter 1 is shipped. In the measurement mode, the urinary sugar level is measured using this measurement reference value.

Particularly, when the reference value setting unit 53 calibrates the sensitivity of the urinary sugar sensor 2 once, the reference fluid detection unit 54 detects that the reference fluid has been additionally applied. In other words, in this urinary sugar meter 1, when the output value judgment unit 52 determines that an output value is not suitable to be set as the measurement reference value, then after this judgment, the user is prompted by way of the display unit 3 to additionally apply reference fluid to the urinary sugar sensor 2. Moreover, the reference fluid detection unit 54 detects when reference fluid has been additionally applied. When calibrating the sensitivity one time, the output acquisition unit 51 uses this additionally applied reference fluid as the object from which another output value is acquired that is different than the aforementioned output value that was previously obtained.

Figure 3:
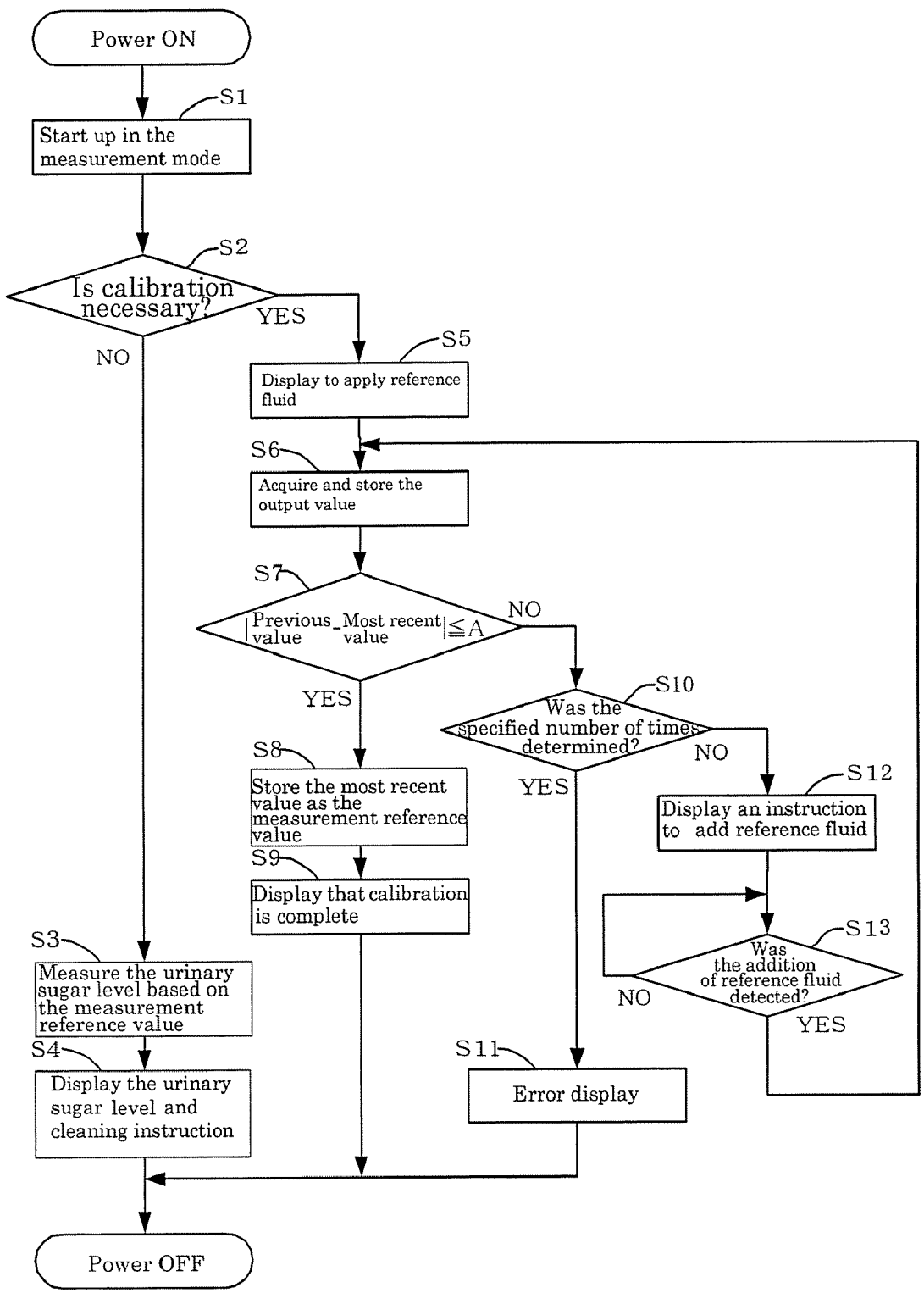
FIG. 3 is a first flowchart for explaining the operation during sensitivity calibration of the urinary sugar meter.

In the urinary sugar meter 1 having this construction, the control unit 5 executes each process according to the flow shown in the flowchart of FIG. 3. When the power to the urinary sugar meter 1 is turned OFF and the user presses the power ON/OFF switch on the operation unit 4, the urinary sugar meter 1 is activated in the measurement mode in step 1 (hereafter, step will be abbreviated as S).

In S2, the control unit (CPU) 5 determines whether or not the sensitivity of the urinary sugar sensor 2 must be calibrated according to the number of times counted by the internal counter that the urinary sugar level has been measured. In S2, whether or not it is necessary to calibrate the sensitivity can also be determined by measuring the amount of time that has elapsed since the previous calibration, and judging whether or not that elapsed time has reached a specified amount of time.

When it is determined in S2 that sensitivity calibration is not necessary, or in other words, when it is determined that the number of times that the urinary sugar level has been measured is less than a specified number of times (S2: NO), in S3, the urinary sugar measurement unit in the control unit 5 measures the urinary sugar level. At this point, the measurement reference value is stored in the reference value memory unit 55, and the urinary sugar measurement unit uses the measurement reference value that is read from the reference value memory unit 55 and measures the urinary sugar level. The method of measuring the urinary sugar level using this measurement reference value is well known, so a detailed explanation of that method is omitted here.

When this measurement of the urinary sugar level is completed, next, in S4, the control unit displays the measured urinary sugar level on the display unit 3, and displays guidance instructing the user to perform the cleaning process. After the user completes the cleaning process, by pressing the power ON/OFF switch, this process ends, and the power to the urinary sugar meter 1 is turned OFF.

On the other hand, in the aforementioned S2, when it is determined that calibration is necessary, or in other words, when the number of times that the urinary sugar level has been measured is equal to or greater than a specified number of times (S2: YES), the urinary sugar meter 1 is switched to the calibration mode, and the sensitivity calibration process starting from S5 is executed.

First, in S5, the control unit 5 performs control to display guidance on the display unit 3 giving instructions to apply reference fluid on the urinary sugar sensor 2. In addition, in S6, the control unit acquires the output value from the urinary sugar sensor 2. In other words, when the user applies reference fluid to the urinary sugar sensor 2 as instructed by the guidance display on the display unit 3, the output value from the urinary sugar sensor 2 is acquired as the measurement value of the reference fluid. At this time, the acquired output value is stored in RAM in time sequence.

Next, in S7, the control unit 5 compares the most recently acquired output value (hereafter, referred to as the 'most recent value') with the output value acquired in the past, and determines whether or not the magnitude of the change between the past output value and the most recent value levels off within an allowable range and whether or not the output value becomes stable. Here, the output value from the previous measurement ('previous value') is used as the past output value, and the most recent value is compared with the previous value to determine whether or not the output value is stable. By doing this, the control unit 5 determines whether or not the most recent value is suitable to be used as the measurement reference value.

In other words, the control unit 5 takes the limit of the allowable value for the change in output of the reference fluid to be A, and determines whether or not the difference between the previous value and most recent value is this allowable limit value A or less. However, when the output that will become the previous value has not been measured, the measurement reference value that is preset at the time the product is shipped and stored in the reference value memory unit 55 is used as the previous value.

When the difference is equal to or less than the allowable limit value A (S7: YES), the control unit 5 determines that the most recent value is suitable to be used as the measurement reference value, and advances to S8. In S8, the measurement reference value that is already stored in the reference value memory unit 55 is replaced by the most recent value as the new measurement reference value. Also, in S9, the control unit 5 displays on the display unit 3 that calibration is complete, and after that, when the user presses the power ON/OFF switch, this process ends, and the power to the urinary sugar meter 1 is turned OFF.

On the other hand, when the difference is greater than the allowable limit value A (S7: NO), the control unit 5 determines that this most recent value is not suitable to be used as the measurement reference value, and advances to S10. For example, when the necessary amount of reference fluid is not applied, there is a high possibility that the obtained most recent value will be determined as not being suitable to be used as the measurement reference value. Furthermore, cumulative reference fluid measurement is performed according to S10 to S13 and S6. In other words, as a result of this cumulative reference fluid measurement, new reference fluid is further applied to the urinary sugar sensor 2, to which the reference fluid that was applied as instructed by the display in S5 is still adhered, and in S6, the output value from the urinary sugar sensor 2 is obtained.

First, in S10, the control unit 5 determines whether or not the suitability judgment performed in S7 has been repeatedly performed a specified number of times. Here, the specified number of times is preset as the upper limit value of the number of times measurement of the reference fluid is performed in one sensitivity calibration. That is, when an output value that is suitable to be used as the measurement reference value is not obtained even though the reference fluid is continuously measured just the specified number of times, the process ends in error. For example, an event such as when the urinary sugar sensor 2 has deteriorated to the extent that it is not capable of sensitivity calibration, or when the measurement mechanism of the urinary sugar meter 1 is defective, or when the user makes a mistake in the operation of the calibration procedure, could cause the number of judgments in S7 to exceed the upper limit.

In this S10, when it is determined that the number of judgments in S7 has reached the specified number of times (S10: YES), in S11, the control unit 5 displays on the display unit 3 that there was an error. After that, when the user presses the power ON/OFF switch, the process ends and the power to the urinary sugar meter 1 is turned OFF.

However, in S10, when it is determined that the number of judgments has not yet reached the specified number of times (S10: NO), in S12, the control unit 5 displays guidance on the display unit 3 giving instructions to further apply reference fluid to the urinary sugar sensor 2 to which reference fluid is already applied. In other words, according to the display in S5, reference fluid has already been applied to the urinary sugar sensor 2 and reference fluid is adhered to the sensor. The user is then instructed to additionally apply more reference fluid to the urinary sugar sensor 2 in this state.

After the user adds and applies reference fluid to this urinary sugar sensor 2, then in S13, the addition of this reference fluid is detected (S13: YES), and the control unit 5 advances to S6. More specifically, the addition of reference fluid in S13 is detected by a small change in the sensor output when reference fluid is additionally applied to the urinary sugar sensor 2. In other words, after the instruction is displayed in S12 to add reference fluid, when the change in the sensor output becomes equal to or greater than a specified threshold value, it is determined that reference fluid was added at the instant that the change in output was detected.

Next, in S6, the output value from the urinary sugar sensor 2 after reference fluid has been additionally applied is acquired, and that output value is then stored. Moreover, this newly acquired output value becomes the most recent value, and the control unit 5 advances to S7 to determine whether or not this most recent value is suitable to be used as the measurement reference value. In one sensitivity calibration of the urinary sugar sensor 2, this judgment of the output value from the urinary sugar sensor 2 and acquiring a new output value is continually repeated until the measurement reference value is finally set and calibration is completed.

In this embodiment, the correlation between the steps shown in the flowchart of FIG. 3 and each of the units shown in the block diagram of FIG. 2, is as described below. In other words, S6 in FIG. 3 corresponds to the output value acquisition unit 51 shown in FIG. 2. S7 in FIG. 3 corresponds to the output value judgment unit 52 in FIG. 2. S8 in FIG. 3 corresponds to the reference value setting unit 53 in FIG. 2. Also, S13 in FIG. 3 corresponds to the reference fluid detection unit 54 in FIG. 2.

When a newly acquired output value from the urinary sugar sensor 2 is determined not to be suitable as the setting for the reference value during one calibration of the sensitivity of the urinary sugar sensor 2 and judgment is performed from an already acquired output value from the urinary sugar sensor 2, after that the urinary sugar meter 1 of this embodiment detects that more reference fluid is additionally applied to the urinary sugar sensor 2 as is without performing the cleaning process. Furthermore, with the reference fluid additionally applied to the sensor, another output value is acquired from the urinary sugar sensor 2. Therefore, compared with a conventional measurement device in which the cleaning process must be performed after an output value has been obtained, it is possible to calibrate the sensitivity of a biosensor more easily and in a shorter amount of time.

Generally, in many conventional measurement devices, when it is determined that sensitivity calibration is necessary, it is not possible to measure the test fluid until that calibration is completed. For example, when there is a notice indicating that it was determined that sensitivity calibration is necessary just at the timing when the test fluid is to be measured, particularly in the case of a urine measurement device, the user had to refrain from urinating until calibration was complete, or the urinary sugar measurement had to be terminated. It is possible to collect the urine in a separate container, however this is troublesome. With this urinary sugar meter 1, sensitivity calibration is performed simply, so these kinds of inconveniences do not occur.

Moreover, with this urinary sugar meter 1, even when the amount of reference fluid that is applied to the urinary sugar sensor 2 during one measurement of the reference fluid is less than the necessary amount, more reference fluid can be added and the reference fluid can be measured again without having to perform the cleaning process. Depending on the circumstances, this is repeated. Particularly, this addition of reference fluid is made possible by the means for detecting the addition of reference fluid. Through repeated addition of reference fluid, it is possible to finally obtain stable output from the urinary sugar sensor 2.

Figure 4A:
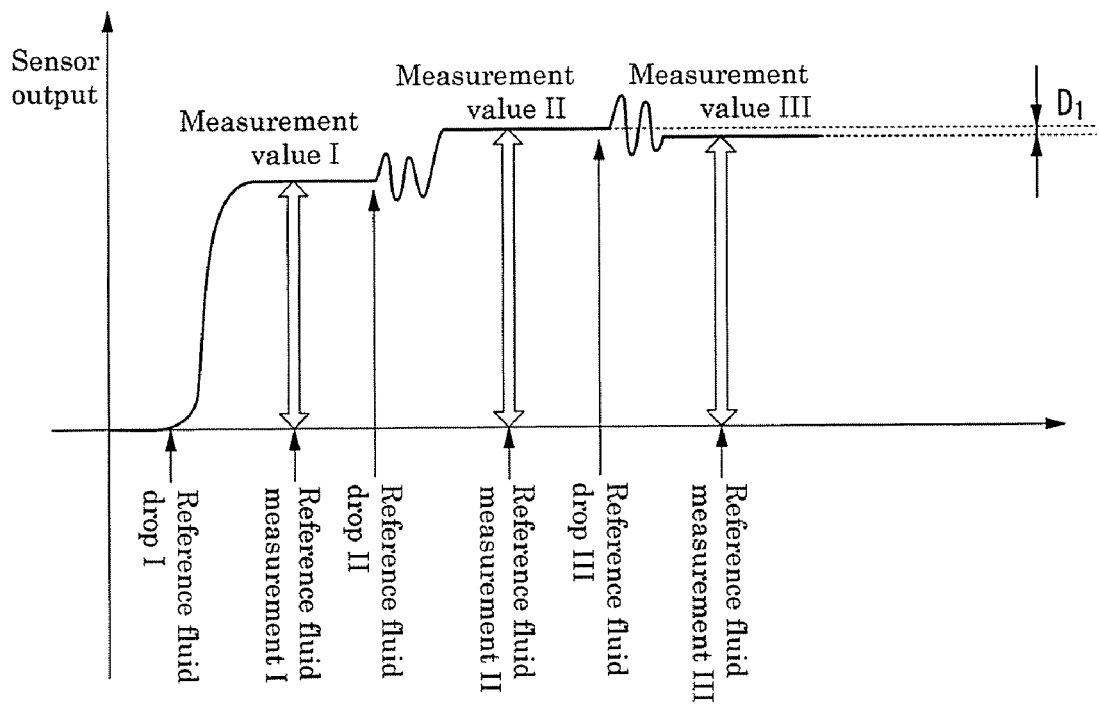
FIG. 4 is a drawing for explaining the effect of sensitivity calibration of the urinary sugar meter.

More specifically, FIG. 4A graphically shows the output of the urinary sugar meter 1, and as shown in FIG. 4A, the difference D1 between the sensor output that is obtained in one reference fluid measurement, and the sensor output that is obtained in the next reference fluid measurement becomes smaller as the addition of reference fluid is repeated.

On the other hand, with a conventional urine measurement device, in one reference fluid measurement, in cases such as when the amount of reference fluid that is applied to the urinary sugar sensor in one reference fluid measurement is less than the necessary amount, the cleaning process is performed in preparation for the next reference fluid measurement.

Figure 4B:
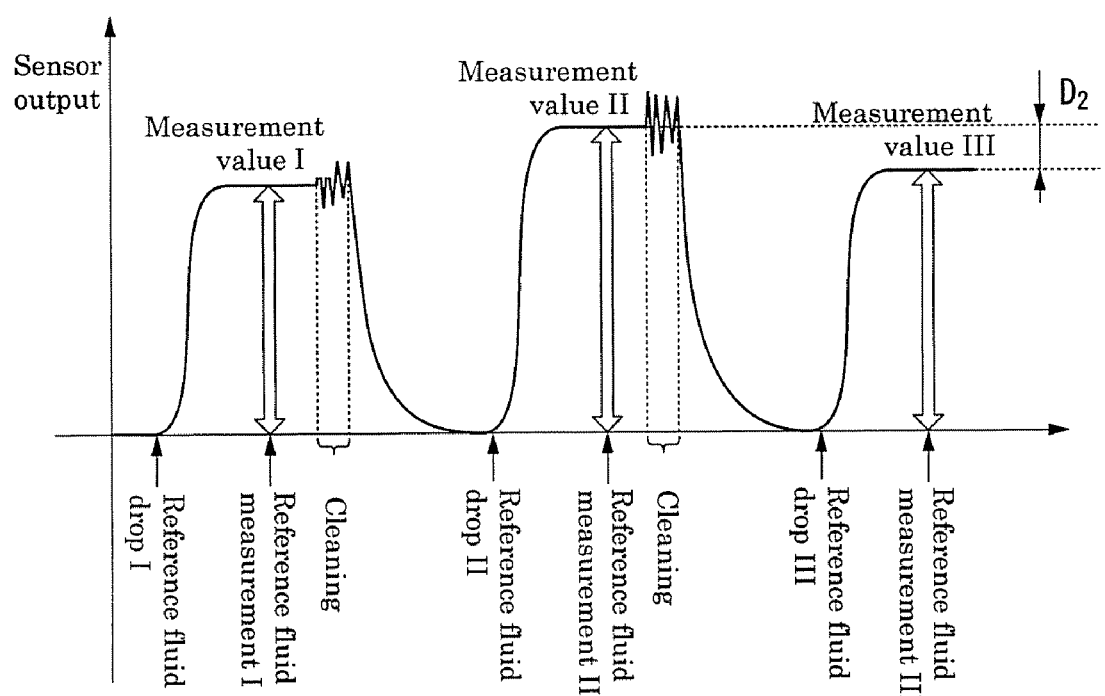

As shown in FIG. 4B, when using a conventional urine measurement device, there is a high possibility that each time reference fluid measurement is performed, there will be larger dispersion in the difference D2 between the sensor output that is obtained in one reference fluid measurement and the sensor output that is obtained in the next reference fluid measurement than with the urinary sugar meter 1 of this invention. Fluid that adheres to the urinary sugar sensor and is saved during the cleaning process changes the physical properties of the reference fluid, and this changes becomes a major cause of the dispersion.

Embodiment 2

Figure 5:
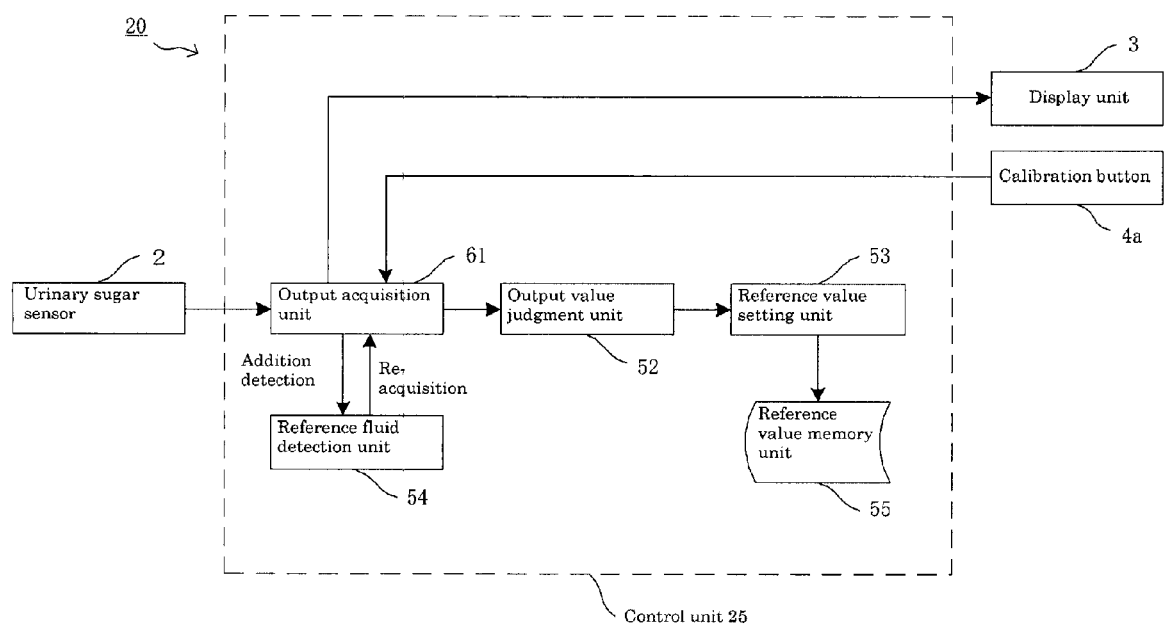
FIG. 5 is a block diagram showing the construction related to the sensitivity calibration of a urinary sugar meter of a second embodiment of the invention.

The urinary meter of a second embodiment of the invention has the construction shown in FIG. 5. That is, this urinary sugar meter 20 has construction similar to the urinary sugar meter 1 of the first embodiment described above, however, in this urinary sugar meter 20 (in the output acquisition unit 61), setting two operating states during execution of the calibration mode, and switching between these two operating states are the main differences from the urinary sugar meter 1 described above. These two operating states are: a preparation state in which output values are not acquired even though reference fluid may be applied to the urinary sugar sensor (non-acquisition state), and a measurement possible state in which output values are acquired when reference fluid is applied to the urinary sugar sensor (acquisition state).

Other than the construction and effect of the urinary sugar meter 20 explained here, the construction and effect of the urinary sugar meter 20 are the same as that of the urinary sugar meter 1 of the first embodiment, so a detailed explanation of them is omitted here. Of the components of the urinary sugar meter 20 shown in FIG. 5, the same reference numbers are used for parts that are identical to those of the first embodiment. Of the steps of the flowchart shown in FIG. 6 of the flow of operations of the urinary sugar meter 20, the same reference numbers are given to steps that are the same as those for the urinary sugar meter 1 shown in FIG. 3.

As shown in FIG. 5, one of the buttons on the operation unit 4 of the urinary sugar meter 20 is a calibration button 4a. This calibration button 4a is used by the user to input an instruction to change the operating state of the urinary meter 20 (output acquisition unit 61) from the preparation state to the measurement possible state just before reference fluid is applied to the urinary sugar sensor 2. The output value acquisition unit 51 changes the operating state from the preparation state to the measurement possible state based on this change instruction. More specifically, after the urinary sugar meter 20 is set to the calibration mode, when the user presses the calibration button 4a one time, the operating state of the urinary sugar meter 20 is changed from the preparation state to the measurement possible state.

Figure 6:
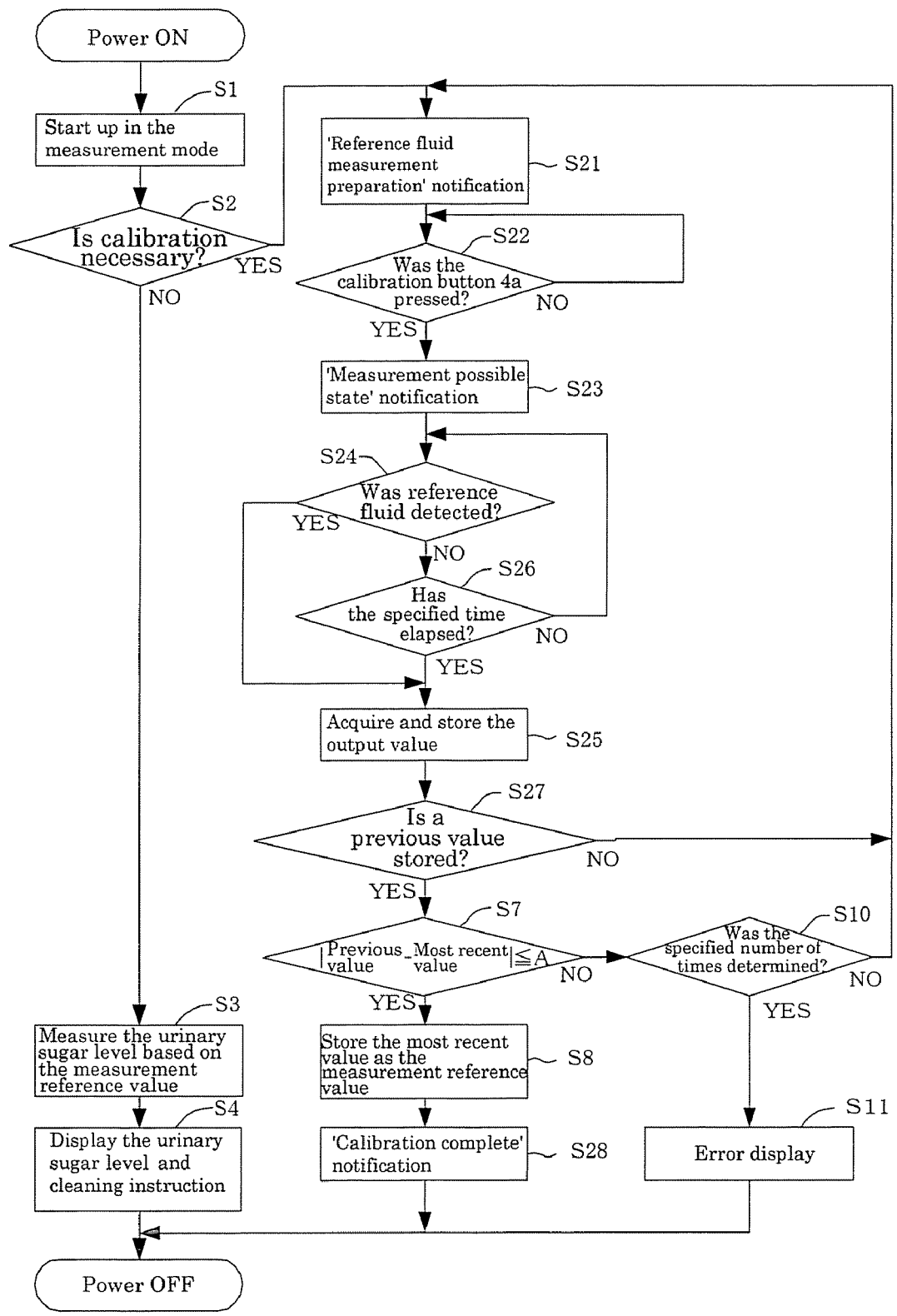
FIG. 6 is a second flowchart for explaining the operation during sensitivity calibration of the urinary sugar meter.

The features of this urinary sugar meter 20 are explained in more detail. In FIG. 6, when it is determined in S2 that the sensitivity of the urinary sugar sensor 2 needs to be calibrated (S2: YES) and the urinary sugar meter 20 is switched to the calibration mode, the process from S21 onward that is related to sensitivity calibration is executed. Differing from the urinary sugar meter 1 of the first embodiment, when the urinary sugar meter 20 is shipped, a measurement reference value for measuring the urinary sugar level in the measurement mode is not stored in the reference value memory unit 55. In other words, after shipment of the product, the user purchases the urinary sugar meter 20, and calibration must be performed even when using the urinary sugar meter 20 for the first time.

Figure 7A:
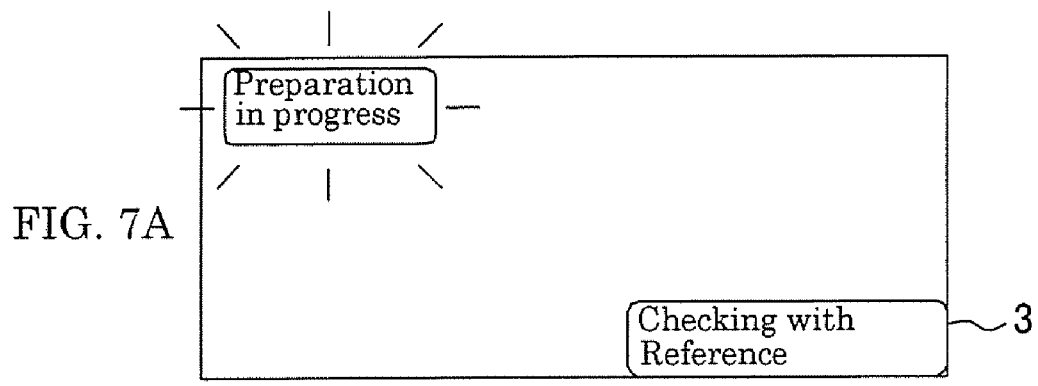
FIGS. 7A to 7D are drawings showing examples of the displays on a display during sensitivity calibration of the urinary sugar meter.

In the sensitivity calibration, first, in S21, the control unit 25 notifies the user that the operating state of the urinary sugar meter 20 is set to the preparation state. For example, the control unit 25 displays the display shown in FIG. 7A on the display unit 3. That is, the flashing display 'Preparation in Progress' is displayed on the display unit 3, and this flashing display notifies the user that the operating state of the urinary sugar meter 20 is set to the preparation state. Moreover, as shown in FIG. 7A, in addition to this display indicating the preparation state, the display, 'Checking with the Reference' is displayed on the display unit 3, and this display notifies the user that the urinary sugar meter 20 is in the calibration mode.

Next, in S22, the control unit 25 determines whether or not the calibration button 4a has been pressed. By pressing the calibration button 4a, the urinary sugar meter 20 (control unit 25) can recognize thereafter when reference fluid is applied to the urinary sugar meter 20 in order to perform sensitivity calibration. In other words, when the calibration button 4a is not pressed (S22: NO), the control unit 25 returns to S22. In that case, the control unit 25 continues to notify that the operating state is the preparation state. On the other hand, when the calibration button 4a is pressed (S22: YES), the operating state of the urinary sugar meter 20 changes from the preparation state to the measurement possible state, and then in S23, the control unit notifies the user by way of the display unit 3 that the operating state of the urinary sugar meter 20 is the measurement possible state.

Figure 7B:
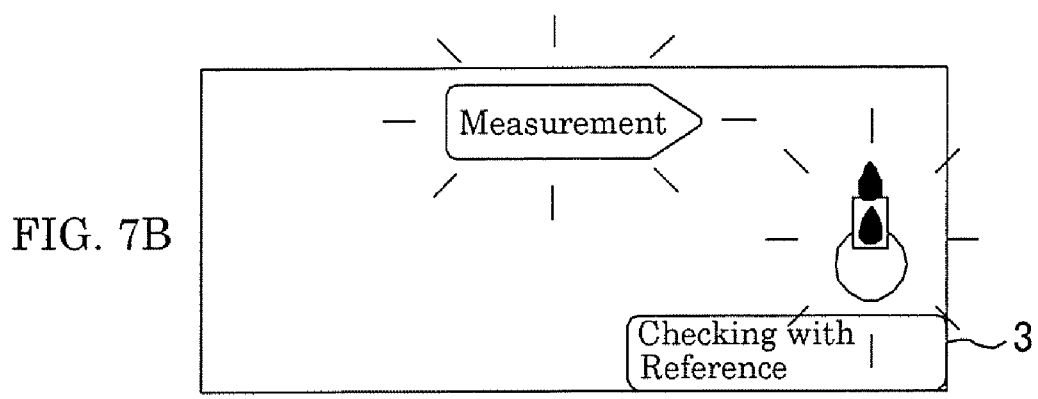

For example, the control unit 25 may display the display shown in FIG. 7B on the display unit 3. At this time, a flashing guidance display 'Measurement' and a flashing drop mark (image of a fluid drop) display are displayed on the display unit 3. This flashing 'Measurement' display indicates that measurement of the reference fluid is possible, and the flashing drop mark prompts the user to apply reference fluid to the urinary sugar sensor 2.

Together with this kind of notification of the measurement possible state, the instant that the operating state changed is stored in memory. In other words, the control unit 25 has an internal timer (not shown in the figure), and is capable of measuring the wait time for waiting for detection of the reference fluid. This wait time can be set to 10 seconds for example, and preferably is set between 5 seconds and 60 seconds.

As shown in FIG. 7B, while the notice is displayed on the display unit 3 that indicates that the operating status is the measurement possible state, in S24, the control unit 25 determines whether or not reference fluid has been applied to the urinary sugar sensor 2. This detection can be according to a small change in sensor output that occurs when reference fluid is applied to the urinary sugar sensor 2.

When it is detected that reference fluid has been applied (S24: YES), in S25, the control unit 25 acquires the output value from the urinary sugar sensor 2 as in the case of the urinary sugar meter 1 of the first embodiment (see S6 of FIG. 3), and stores that output value in RAM in time sequence. When acquiring this output value, the control unit 25 can notify the user that the urinary sugar sensor 2 is measuring the urinary sugar level.

Figure 7C:
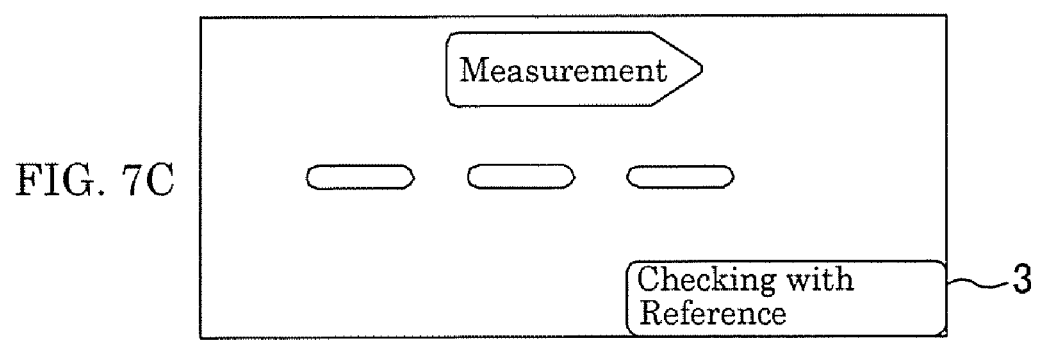

For example, the control unit 25 displays the display shown in FIG. 7C on the display unit 3. In other words, here the drip mark display is no longer displayed, and the 'Measurement' guidance display changes from a flashing display to being continuously lit up, and furthermore, measurement bars (three bars that run horizontally) appear. At first all three of the measurement bars are lit up, and the number of lit up measurement bars decreases at set intervals. When all three of the measurement bars have gone off, all three of the measurement bars will be lit up again. This kind of measurement bar display continues until another display, such as that in S23, S28 or S11, is displayed.

After the output value has been acquired and stored in memory in S25, the control unit 25 changes the operating state of the urinary sugar meter 20 from the measurement possible state to the preparation state, and prevents the acquisition of output values. After the processing in S25, the control unit 25 advances to S27.

On the other hand, in S24, when application of reference fluid was not detected (S24: NO), in S26, the control unit 25, according to the clock count of the timer, further determines whether or not the wait time has become a specified time. When the wait time has not reached the specified time (S26: NO), the control unit 25 returns to S24 and waits for reference fluid to be detected. On the other hand, when the wait time has reached the specified time (S26: YES), the control unit 25 advances to S25 and performs the processes described above such as acquiring the output value of the urinary sugar sensor 2.

At this point, after a specified amount of time has elapsed from the time when the operating state of the urinary sugar meter 20 changes from the preparation state to the measurement possible state, the output value from the urinary sugar sensor 2 is acquired. That is, it is considered that reference fluid has been applied to the urinary sugar sensor 2 even though the application of reference fluid was not detected in S24. After that, the control unit 25 advances to S27.

By regarding that reference fluid has been applied to the urinary sugar sensor 2 after a specified amount of time has elapsed, it is possible to avoid the operation error of the urinary sugar meter 20 not being able to detect the output value from the urinary sugar sensor 2, even though the user has applied reference fluid.

In S27, the control unit 25 determines whether or not a previous value is stored in memory with respect to the acquired output value, or in other words, the most recent value. When the previous value is stored in memory (S27: YES), the process from S7 onward is executed.

In other words, in S7, the control unit 25 determines whether the most recent value is suitable to be used as the measurement reference value as in the case of the urinary sugar meter 1 of the first embodiment. When the most recent value is not suitable to be used as the measurement reference value (S7: NO), then, as in the case of the urinary sugar meter 1, the control unit 25 determines in S10 whether the number of times the suitability of the most recent value has been judged has reached a specified number of times, and in S11, displays an error display or the like.

Figure 7D:
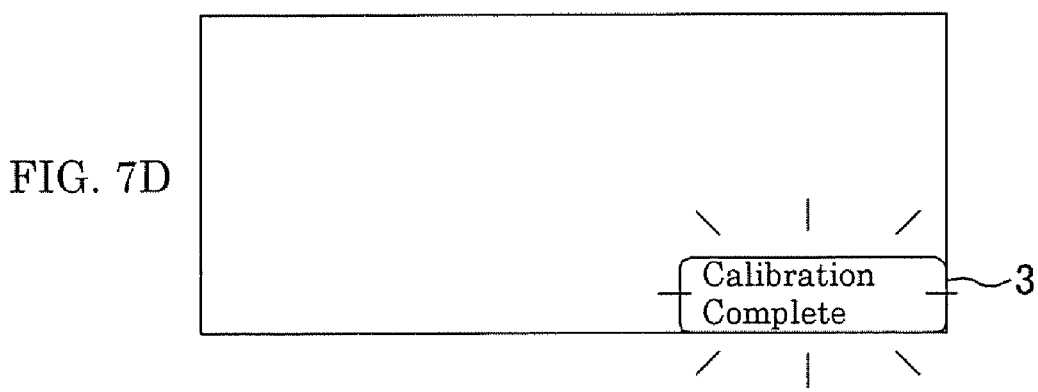

On the other hand, when the most recent value is suitable to be used as the measurement reference value (S7: YES), then as in the case of the urinary sugar meter 1, in S8 the control unit 25 stores the most recent value in memory as the measurement reference value, and in S28 displays a display indicating that calibration is complete. This calibration complete display may be a display as shown in FIG. 7D. That is, here, instead of the 'Checking with the Reference' text display in the display of S21 (see FIG. 7A), the display of S23 (see FIG. 7B) and the display in S25 (see FIG. 7C), a flashing text display 'Calibration Complete' is displayed. This 'Calibration Complete' display notifies the user that calibration is complete.

Contrary to the process performed from S7 onward, in S27, when the most recent value is not stored in memory (S27: NO), that is, when the reference fluid measurement is performed for the first time in a sensitivity calibration, processing proceeds as though the output value (most recent value) is not suitable to be used as the measurement reference value. In other words, in this case, in S7 determining whether or not the most recent value is suitable to be used as the measurement reference value is not performed, and from S21 onward, the second reference fluid measurement is performed while additionally applying reference fluid.

In the first reference fluid measurement in one sensitivity calibration, it is presumed that the output value from the urinary sugar sensor 20 is not stable. Since the unstable first output value is not used as the measurement reference value setting, the reliability of the measurement reference value that is set in sensitivity calibration is improved.

In each of the steps of the flowchart of FIG. 6, the correlation with each of the parts of the block diagram of FIG. 5 is as follows. In FIG. 6, S25 and S26 correspond to the output value acquisition unit 61 in FIG. 5. S7 and S27 in FIG. 6 correspond to the output value judgment unit 52 in FIG. 5. S8 in FIG. 6 corresponds to the reference value setting unit 53 in FIG. 5. Also, S24 in FIG. 6 (particularly from the second time on) corresponds to the reference fluid detection unit 54 in FIG. 5.

As in the case of the urinary sugar meter 1 of the first embodiment, with this urinary sugar meter 20 as well, when it is determined from an output value already obtained from the urinary sugar sensor 2 that the output value of the urinary sugar sensor 2 is not suitable to be used as the reference value in one sensitivity calibration of the urinary sugar sensor 2, after that reference fluid is additionally applied to the urinary sugar sensor 2 and detected without performing the cleaning process. Therefore, when compared with a conventional measurement device in which the cleaning process must be performed after each time an output value is obtained, it is possible to calibrate the sensitivity of a biosensor more easily and in a shorter amount of time.

Other Embodiments

The invention was explained using detailed embodiments, however, the present invention is not limited to the embodiments described above, and may be changed within a range that does not depart from the scope of the invention.

A. For example, in the second embodiment described above, even though reference fluid is not detected, the specified time from the time when the measurement possible state is set in S23 of FIG. 6 until the output value of the urinary sugar sensor 2 is acquired is fixed at 10 seconds. Differing from this, it is also possible to use a variable value as this specified time. For example, in the first judgment in S26 in a sensitivity calibration, the specified time can be taken to be 30 seconds, and this specified time can be taken to be 5 seconds for the second judgment in S26 and later.

Here, (1) during the first time, the user is not immediately prepared to apply reference fluid, and requires time after being notified of the measurement possible state; (2) from the second time on, the user is prepared to additionally apply reference fluid in that state, so it is presumed that a long time is not required after notification. By doing this, acquisition of the output value from the urinary sugar sensor 2 can be performed smoothly.

B. Moreover, in the first embodiment described above, in S7 of FIG. 3, depending on whether or not the difference between the most recent value and the previous value is equal to or less than an allowable limit value A, whether or not the most recent value is suitable for use as the measurement reference value was determined. Instead of using the difference between the most recent value and the previous value, it is also possible to use the difference between the most recent value and the measurement value from the measurement two times previous, which is the value previous to the previous value.

Furthermore, without relying on the judgment in S7, it is also possible to use a plurality of output values from the urinary sugar sensor 2 in setting the measurement reference value. For example, (1) in one sensitivity calibration, reference fluid measurement is repeated a specified number of times, two times or greater; (2) of the output values that are obtained from this specified number of times, output values that are determined to be suitable as the setting for the measurement reference value are taken to be temporary reference values; (3) the average of all of the obtained temporary reference values is found; (4) the average value is taken to be the measurement reference value and is stored in the reference value memory unit 55.

Of the temporary reference values obtained in (2) above, it is also possible to find the average of the two temporary reference values whose difference is the smallest among the temporary reference values, and take this average value as the measurement reference value and store it in the reference value memory unit 55. When finding the average value, an error display can be displayed as in S11 of FIG. 3 when no temporary reference values are obtained.

C. In S13 of FIG. 3 of the first embodiment and S24 of FIG. 6 of the second embodiment, the additional application of reference fluid to the urinary sugar sensor 2 is detected by minute change in the output value of the urinary sugar sensor 2. Differing from this, it is possible to use a temperature sensor that detects the temperature of the urinary sugar sensor 2, and to detect the addition of reference fluid by detecting change in the detected temperature of the urinary sugar sensor 2.

Moreover, it is possible to use an impact sensor that detects physical impact to the urinary sugar sensor 2, and to detect the addition of reference fluid by that detected impact.

In the case of detecting the addition of reference fluid by using a temperature sensor or impact sensor, it is possible to accurately detect the addition of reference fluid even when there is no change in the output value of the urinary sugar sensor after reference fluid is added. Also, in this case, it is difficult for the problem of falsely detecting changes in output of the urinary sugar sensor to occur due to external noise or the like as the addition of reference fluid, even though reference fluid has not been added.

Furthermore, it is possible to include an addition confirmation button on the operation unit 4 that is used by the user in order to input confirmation immediately after reference fluid has been applied to the urinary sugar sensor 2 that reference fluid has been applied to the urinary sensor 2. At this point, the addition of reference fluid is detected when the user actually presses this addition confirmation button in order to confirm that reference fluid has been added.

When using the addition confirmation button, in addition to the effect that is obtained when using the aforementioned temperature sensor or the like, this button has the merit in that it is easy for the user to know which operation in a specified operating procedure is currently being performed.

By suitably combining a plurality of detection means to detect the addition of reference fluid, it is possible to make the detection even more effective.

D. In the first and second embodiment, the biosensor was a urinary sugar sensor, however, the biosensor can also be another sensor that requires calibration using a reference fluid. An example of a portable urinary sugar meter was given as the test fluid measurement device, however, it is also possible to use another installable type of test fluid measurement device. The test fluid measurement device referred to here includes clinical testing devices.

What is claimed is:

1. A test fluid measurement device comprising:
a biosensor that measures the amount of a certain substance that is contained in a test fluid;
output acquisition means for acquiring the output value of said biosensor when a reference fluid containing said certain substance that is set to a specified density is applied to said biosensor during a sensitivity calibration of said biosensor;
setting means for calibrating the sensitivity of said biosensor by setting a reference value that will be a reference for measurement by said biosensor using said output value that was acquired from said biosensor by said output acquisition means;
judgment means for determining whether or not a said output value that is newly acquired from said biosensor by said output acquisition means during said sensitivity calibration by said setting means is suitable to be used as the setting for said reference value based on a previous output value that has already been acquired from said biosensor by said output acquisition means; and
detection means for detecting when said reference fluid, which is the subject of acquiring another output value by said output acquisition means, is additionally applied to said biosensor after said judgment means determines that an output value is not suitable as the setting for said reference value,
wherein when said judgment means has determined that the new output value is not suitable as the setting for said reference value, the additional application of more reference fluid to said biosensor is detected without performing a cleaning process.

2. The test fluid measurement device of claim 1, wherein said setting means sets said output value from said biosensor, which was determined by said judgment means to be suitable as the setting for said reference value, as said reference value.

3. The test fluid measurement device of claim 1, wherein said setting means sets the average of said output values, which were acquired by said output acquisition means a specified number of times and were determined by said judgment means to be suitable as the setting for said reference value, as said reference value.

4. The test fluid measurement device of claim 1, wherein said judgment means determines that said output value from said biosensor that was acquired the first time by said output acquisition means during said sensitivity calibration by said setting means is not suitable as the setting for said reference value.

5. The test fluid measurement device of claim 1, wherein said detection means detects that said reference fluid has been additionally applied to said biosensor due to change in the output value from said biosensor that is acquired by said output acquisition means.

6. The test fluid measurement device of claim 1, wherein said detection means comprises temperature detection means for detecting the temperature of said biosensor;
wherein said temperature detection means detects that said reference fluid has been additionally applied to said biosensor due to change in the temperature of said biosensor.

7. The test fluid measurement device of claim 1 wherein said detection means comprises impact detection means for detecting physical impact that is applied to said biosensor;
wherein said impact detection means detects that said reference fluid has been additionally applied to said biosensor due to impact to said biosensor.

8. The test fluid measurement device of claim 1, further comprising
addition confirmation means for a user to input confirmation that said reference fluid has been additionally applied to said biosensor; wherein
said detection means detects that said reference fluid has been additionally applied to said biosensor due to said addition confirmation that is input from said addition confirmation means.

9. The test fluid measurement device of claim 1, wherein said output acquisition means has two operating states; a non acquisition state in which said output value from said biosensor is not acquired even though said reference fluid is applied, and an acquisition state in which said output value from said biosensor is acquired when said reference fluid is applied; and comprises an instruction input means for a user to input an instruction to change said operating state of said output acquisition means from said non acquisition state to said acquisition state; and wherein said output acquisition means changes said operating state from said non acquisition state to said acquisition state based on said change instruction that is input from said instruction input means.

10. The test fluid measurement device of claim 9, wherein said output acquisition means acquires an output value from said biosensor after a specified amount of time has elapsed from the instant when said operating state of said output acquisition means changes from said non acquisition state to said acquisition state.

11. The test fluid measurement device of claim 9, further comprising notification means for notifying that said operating state of said output acquisition means is either said non acquisition state or said acquisition state.

12. The test fluid measurement device of claim 1, wherein the additional application of more reference fluid to said biosensor is carried out manually by a user.

13. The test fluid measurement device of claim 1, wherein the device is portable.

14. The test fluid measurement device of claim 1, wherein the certain substance is sugar content in the urine of the test fluid, and the biosensor is a urine sugar sensor.

15. The test fluid measurement device of claim 1, wherein the judgment means makes the process end in error when said output value is not obtained even though the reference fluid is continuously measurement a specified number of times.

16. The test fluid measurement device of claim 1, wherein the judgment means determines whether or not the difference between the previous output value and said newly acquired output value which the output value is an allowable limit value or less and judges whether or not said sensitivity calibration is suitable, wherein the judgment means uses a measurement reference value that is present when said previous value has not been measured.

17. The test fluid measurement device of claim 10, wherein the specified amount of time to acquisition of the output value is a variable value, and the variable value is shorter for the second judgment and later.

18. The test fluid measurement device of claim 11, wherein said output acquisition means acquires an output value from said biosensor after a specified amount of time has elapsed from the instant when said operating state of said output acquisition means changes from said non acquisition state to said acquisition state, and wherein the specified amount of time to acquisition of the output value, and the variable value is shorter for the second judgment and later.

19. A sensitivity calibration method for calibrating the sensitivity of a biosensor, comprising steps of:

providing a biosensor that measures the amount of a certain substance that is contained in a test fluid;

acquiring the output value of said biosensor when a reference fluid containing said certain substance that is set to a specified density is applied to said biosensor during a sensitivity calibration of said biosensor;

setting a reference value that will be a reference for measurement by said biosensor using said acquired output value;

determining whether or not a said output value that is newly acquired from said biosensor during said sensitivity calibration is suitable to be used as the setting for said reference value based on a previous output value that has already been acquired; and detecting when said reference fluid, which is the subject of acquiring another output value, has been additionally applied to said biosensor after an output value is determined not to be suitable as the setting for said reference value, wherein when said determining step has determined that the output value is not suitable as the setting for said reference value, the additional application of more reference fluid to said biosensor is detected without performing a cleaning process.

20. The sensitivity calibration method of claim 19, wherein the additional application of more reference fluid to said biosensor is carried out manually by a user.

* * * * *